(12) United States Patent
Novak et al.

(10) Patent No.: US 10,180,435 B2
(45) Date of Patent: Jan. 15, 2019

(54) METHOD OF SURFACE MODIFICATION BY PROTEINS FOR ANALYTE PRECONCENTRATION FOR DESORPTION-IONIZATION MASS SPECTROMETRY TECHNIQUES AND FOR IMMUNOCHEMICAL ASSAYS

(71) Applicants: Petr Novak, Dolni Brezany (CZ); Michael Volny, Prague (CZ); Petr Pompach, Mratin (CZ); Viktor Ruzicka, Rymarov (CZ)

(72) Inventors: Petr Novak, Dolni Brezany (CZ); Michael Volny, Prague (CZ); Petr Pompach, Mratin (CZ); Viktor Ruzicka, Rymarov (CZ)

(*) Notice: Subject to any disclaimer, the term of this patent is extended or adjusted under 35 U.S.C. 154(b) by 140 days.

(21) Appl. No.: 15/511,680

(22) PCT Filed: Sep. 16, 2015

(86) PCT No.: PCT/CZ2015/000107
§ 371 (c)(1),
(2) Date: Mar. 16, 2017

(87) PCT Pub. No.: WO2016/041531
PCT Pub. Date: Mar. 24, 2016

(65) Prior Publication Data
US 2017/0242030 A1    Aug. 24, 2017

(30) Foreign Application Priority Data
Sep. 16, 2014 (CZ) .................................... 2014-631

(51) Int. Cl.
| | | |
|---|---|---|
| *G01N 1/40* | (2006.01) | |
| *G01N 33/68* | (2006.01) | |
| *H01J 49/00* | (2006.01) | |
| *H01J 49/04* | (2006.01) | |

(52) U.S. Cl.
CPC ......... *G01N 33/6851* (2013.01); *G01N 1/405* (2013.01); *G01N 33/6848* (2013.01); *H01J 49/0031* (2013.01); *H01J 49/0418* (2013.01); *G01N 2560/00* (2013.01)

(58) Field of Classification Search
None
See application file for complete search history.

(56) References Cited

U.S. PATENT DOCUMENTS

| | | | |
|---|---|---|---|
| 6,579,719 B1 | 6/2003 | Hutchens et al. | |
| 6,844,165 B2 | 1/2005 | Hutchens et al. | |
| 6,881,586 B2 | 4/2005 | Hutchens et al. | |
| 9,358,573 B2* | 6/2016 | Volny .................... | C07K 1/22 |
| 2007/0059769 A1 | 3/2007 | Blixt et al. | |
| 2008/0116367 A1 | 5/2008 | Kim et al. | |

FOREIGN PATENT DOCUMENTS

| | | |
|---|---|---|
| EP | 1764824 A2 | 3/2007 |
| WO | 2005088310 A2 | 9/2005 |
| WO | 2012079549 A2 | 6/2012 |

OTHER PUBLICATIONS

Blacken, Grady R. et al., "In Situ Enrichment of Phosphopeptides on MALDI Plates Functionalized by Reactive Landing of Zirconium (IV)-n-Propoxide Ions," Analytical Chemistry (2007) 79(14):5449-5456.
Farah, M.A. et al., "Analysis of glycated insulin by MALDI-TOF mass spectrometry," Biochim. Biophys. Acta. (2005) 269-282.
Gontarev, S. et al.., "Application of phenylboronic acid modified hydrogel affinity chips for high-throughput mass spectrometric analysis of glycated proteins," Rapid Communications in Mass Spectrometry (2007) 21:1-6.
Hutchens, T.W. et al., "New Desorption Strategies for the Mass Spectrometric Analysis of Macromolecules," Rapid Commun Mass Spectrom (1993) 7(7):576-580.
International Search Report in International Patent Application No. PCT/CZ2015/000107, dated Feb. 1, 2016, 3 pgs.
Jaworek, A., "Electrospray droplet sources for thin film deposition," Journal of Materials Science (2007) 42(1):266-297.
Krásný, Lukáš et al., "High-throughput workflow for identification of phosphorylated peptides by LC-MALDI-TOF/TOF-MS coupled to in situ enrichment on MALDI plates functionalized by ion landing," Journal of Mass Spectrometry (2015) 50(6):802-811.
Krásný, Lukáš et al., "In-situ enrichment of phosphopeptides on MALDI plates modified by ambient ion landing," Journal of Mass Spectrometry (2012) 47(10):1294-1302.
Law, K.P. et al., "Recent advances in SALDI-MS techniques and their chemical and bioanalytical applications," Analytical and Bioanalytical Chemistry (2011) 399(8)2597-2622.
Lee, Bumhwan et al., "Fabrication of a protein film by electrospray deposition method and investigation of photochemical properties by persistent spectral hole burning," Biomaterials (2003) 24(12):2045-2051.

(Continued)

*Primary Examiner* — Lisa V Cook
(74) *Attorney, Agent, or Firm* — Wood Herron & Evans LLP

(57) ABSTRACT

A method for modification of solid substrates with proteins for efficient surface preconcentration of an analyte from multi-component samples before the detection based on desorption-ionization mass spectrometry and immunochemical assays. The claimed subject is a method of modification of surfaces used as substrates for desorption-ionization mass spectrometry and immunochemical assays. The method is based on electronebulization (electrospraying) of protein solution, depending on the intended application either enzymes, lectins, or antibodies. The formed charged electrospray is dried in real time by its passing through an evaporation compartment and the resulting beam of desolvated ions impacts onto the surface and binds to it firmly. Such modified surface can be then used for a selective interaction with an affinity partner of the deposited protein, its preconcentration or enzymatic modification followed by an analysis by means of desorption-ionization mass spectrometry or immunochemical assays.

12 Claims, 16 Drawing Sheets

(56) References Cited

OTHER PUBLICATIONS

Figure 1:
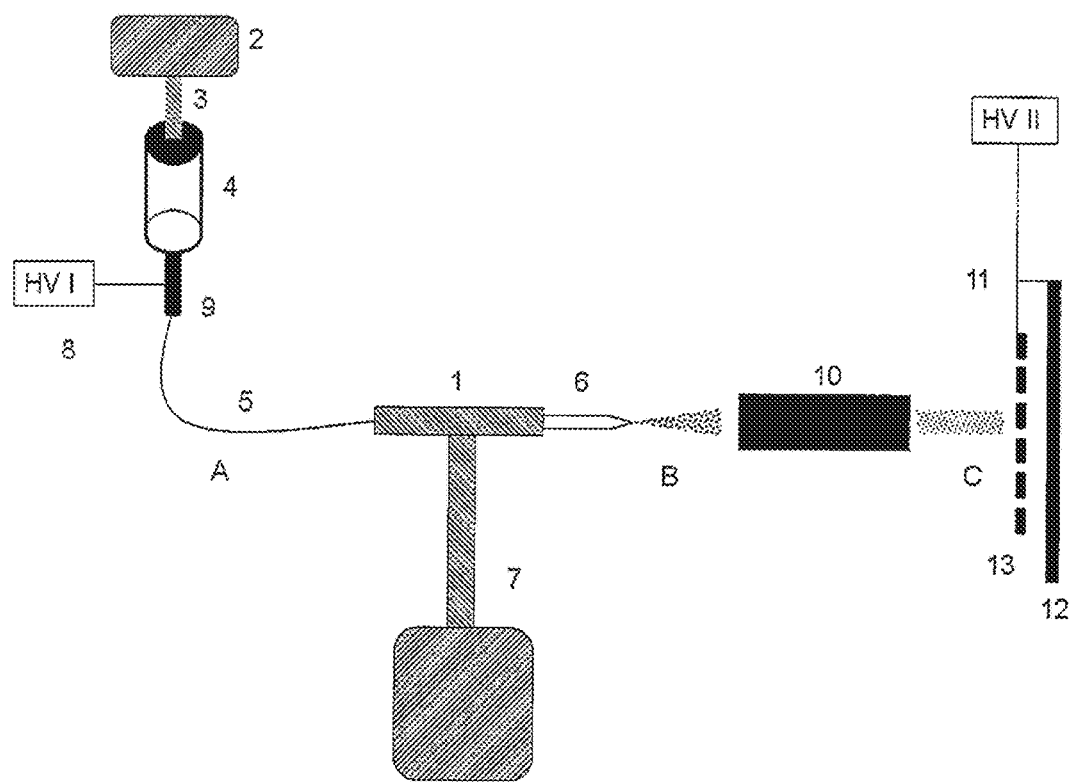

Lee, J.H. et al., "Immobilization of Aminophenylboronic Acid on Magnetic Beads for the Direct Determination of Glycoproteins by Matrix Assisted Laser Desorption Ionization Mass Spectrometry," J. Am. Soc. Mass Spectrom. (2005) 16(9):1456-1460.
Liu, X-C et al., "Studies on Oriented and Reversible Immobilization of Glycoprotein using Novel Boronate Affinity Gel," J. Mol. Recognit. (1996) 9:462-467.
Morozov, V.N. et al., "Electrospray Deposition as a Method to Fabricate Functionally Active Protein Films," Analytical Chemistry (1999) 71:1415-1420.
Morozov, V.N., "Electrospray Deposition of Biomolecules," Adv. Biochem. Eng. Biotechnol. (2010) 119: 115-162.
Pompach, Petr et al., "Planar Functionalized Surfaces for Direct Immunoaffinity Desorption/Ionization Mass Spectrometry," Clinical Chemistry (2016) 62(1):270-278.
Shmanai, V. et al.., "Modification of aluminum chips for LDI mass spectrometry of proteins," Journal of Mass Spectrometry (2007) 42:1504-1513.
Tang, N. et al., "Current developments in SELDI affinity technology," Mass Spectrometry Reviews (2004) 23(1):34-44.
Tubbs, Kemmons A. et al., "High-throughput MS-based protein phenotyping: Application to haptoglobin," Proteomics (2005) 5(18):5002-5007.
Volny, M. et al., "Preparative Soft and Reactive Landing of Multiply Charged Protein Ions on a Plasma-Treated Metal Surface," Anal. Chem. (2005) 77:4890-4896.
Written Opinion in International Patent Application No. PCT/CZ2015/000107, dated Feb. 1, 2016, 6 pgs.

\* cited by examiner

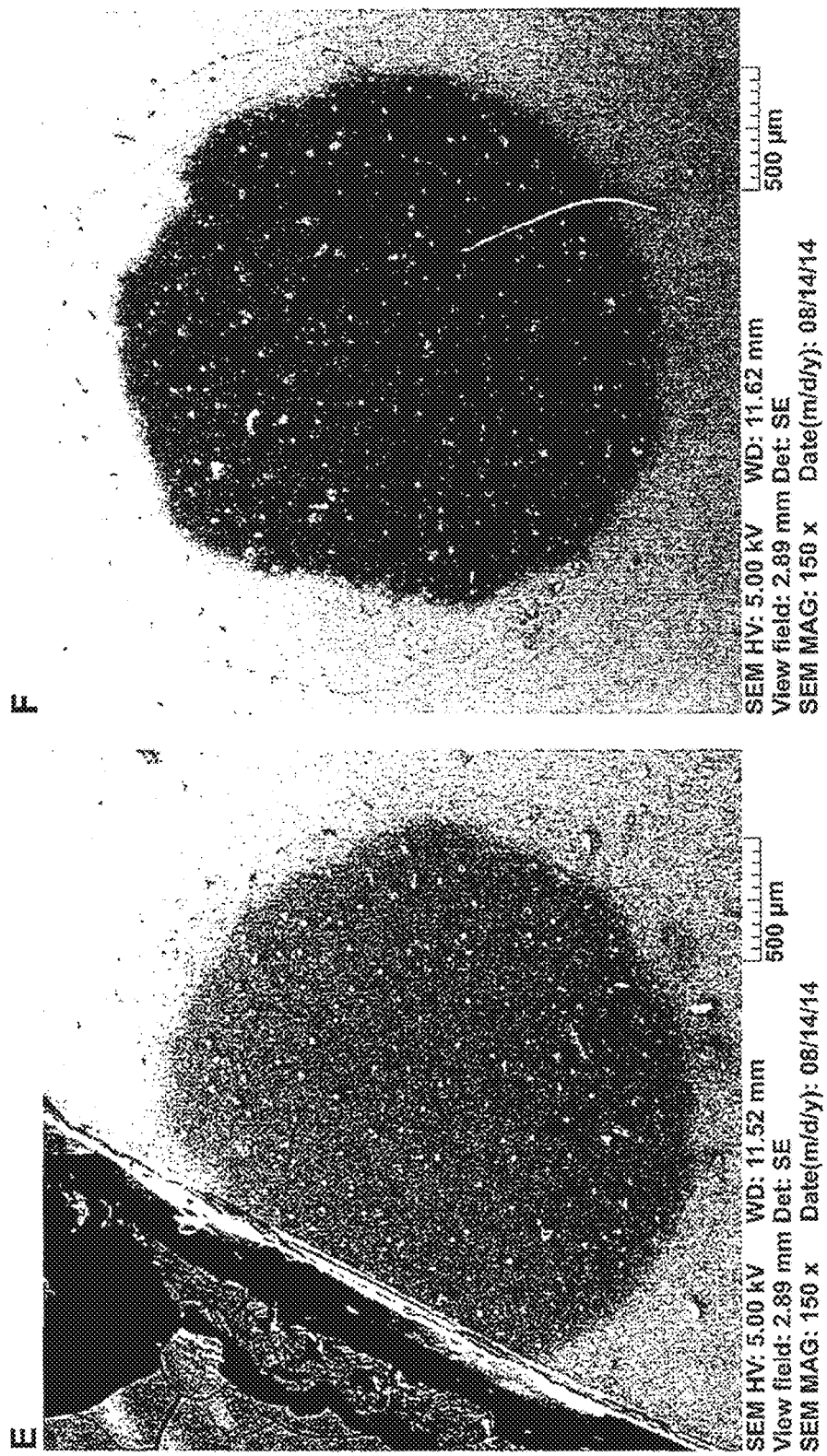

METHOD OF SURFACE MODIFICATION BY PROTEINS FOR ANALYTE PRECONCENTRATION FOR DESORPTION-IONIZATION MASS SPECTROMETRY TECHNIQUES AND FOR IMMUNOCHEMICAL ASSAYS

This application is a 371 of PCT/CZ2015/000107 filed Sep. 16, 2015 and foreign application CZECHIA PV 2014-631 filed Sep. 16, 2014

FIELD OF THE INVENTION

The invention relates to a method of surface modification by proteins for efficient selective preconcentration of an analyte from complex mixtures before a detection based on desorption-ionization mass spectrometry and immunochemical assays.

BACKGROUND OF THE INVENTION

Modern biochemical assays used in human and veterinary medicine, research, and industry, are very often based on an interaction between a protein and its biological partner. If the protein is an antibody and the analyte to be determined is its corresponding antigen, the assays are commonly called immunotests or immunoassays. In the conventional arrangement, the protein is anchored to a solid surface (for example a plate or a bead) which enables the manipulation after the analyte had been bound to the protein. The beads with protein-analyte complex can be removed from the solution of a mixed sample, or the residual sample can be washed out from the plate before the detection, while the analyte remains anchored on the surface due to the interaction with the protein. The main advantage of this type of assays is their high specificity and enrichment of determined analyte which considerably helps enhancing the limit of detection and limit of quantification.

A wide variety of methods and techniques can be used for determination of an analyte enriched by means of an interaction with a protein. One of the key requirements is the compatibility with the used surface that serves as a substrate for the analysis. Desorption-ionization mass spectrometry is an important alternative to the current methods of detection, such as chemiluminescence, fluorescence, or radiation. In this technique, the analyte is desorbed from the surface while it is simultaneously ionized, and it is subsequently introduced to the mass analyzer and detected. Desorption ionization is usually carried out by a laser beam, but charged or neutral particles beam, plasma or electric discharge, electric field, stream of hot solvent steam, or beam of charged solvent droplets can be used instead. Compare to prevalent fluorescence or radiation detection the desorption-ionization mass spectrometry has the advantage of high specificity and possibility to get more information about the detected ion obtained by ionization of the analyte molecule than the conventional detection techniques.

The first technology based on modified surfaces for the desorption-ionization mass spectrometry was named SELDI (Surface-Enhanced Laser Desorption/Ionization) (Hutchens T W and Yip T T. "New desorption strategies for the mass spectrometric analysis of macromolecules." Rapid Commun Mass Spectrom 7: 576-580 (1993). The less specific SELDI surfaces that bind the whole groups of analytes were developed, with different organic materials on the surface ((a) Tang N, Tornatore P, Weinberger S R (2004). "Current developments in SELDI affinity technology". *Mass spectrometry reviews* 23 (1): 34-44; (b) Law K. P, Larkin S. R.: Anal Bioanal Chem (2011) 399:2597-2622), under many trade names (for example CM10—weak ion-exchange resin, Q10—strong ion-exchange resin, H50—hydrophobic reverse chromatography surface, IMAC30—phosphopeptides binding surface). More specific SELDI surfaces with bound proteins, antibodies included, are based on the usage of gold layer that is able to bind a wide variety of biological molecules due to the gold reactivity (U.S. Pat. No. 6,579, 719; U.S. Pat. No. 6,844,165; U.S. Pat. No. 6,881,586). This process has the disadvantage of nonspecific bonding of all proteins in a sample onto the primary gold surface. This leads to reduction of detection specificity for the particular analyte, because not only the appropriate partner of an anchored protein binds onto the surface, but also many other molecules that can react with the gold surface. Alternatively, a molecule can be attached to a surface with the use of surface derivatization, for example by N-hydroxysuccinimide that can form the bond with a biological molecule via any nonprotected amine group (US20070059769 A1, WO2005088310A2). Substrate modification with phenylboronic acid, carboxyarylboronic acid, or aminophenylboronic acid is another chemical modification that enables binding of proteins. The surfaces modified in this way can be used as substrates for immunoassays as well (Liu and Scouten, J Mol Recognit. 1996 September-December; 9(5-6):462-7; Lee et al, S Am Soc Mass Spectrom. 2005 September; 16(9):1456-60, Farah et al, Biochim Biophys Acta. 2005 Oct. 10; 1725(3):269-82). The surfaces modified with phenylboronic acid or carboxyarylboronic acid were used for binding the glycosilized proteins from a sample, followed by desorption-ionization mass spectrometry detection, more particularly MALDI-MS (Gontarev et al. Rapid Communications in Mass Spectrometry 2007, 21(1): 1-6 and Shmanai Journal of Mass Spectrometry 2007 November, 42 (11): 1504-1513 and US 20080116367 A1). The coupling with the desorption-ionization mass spectrometry can be performed better with the use of techniques that enable binding the protein directly onto a metallic surface (the substrate for mass spectrometry measurement). The reason is that bare metal surface with no chemical interlayer, provides better charge transfer and thus more efficient ionization. However, most metals (for example stainless steel or aluminium) cannot be modified directly with proteins because no surface reaction occurs under normal conditions in solution. (Volny M. et al. Anal Chem 2005 August; 77(15):4890-6) used the process called reactive landing for modification of the stainless steel surfaces with proteins. This method of surface treatment was performed under vacuum and the plasma pre-treated surface was exposed to bombardment by desolvated ions; these ions were obtained by soft electrospray ionization of corresponding protein solutions. In the process of reactive landing according to Volny et al. (Volny M. et al. Anal Chem 2005 August; 77(15):4890-6), the charged protein ions, that hit the surface to be modified, translated in the vacuum environment with the mean free path sufficient to allow acceleration of the charged protein ions by external electrostatic field (up to 20V) and thus to reach considerably hyperthermal energy. At the time of impact, 20V of acceleration corresponds to more than thousand fold of average translational kinetic energy at the room temperature (according to the approximation based on kinetic theory of gases). Thus, the surface is modified due to the ion energy at the moment of ion impact on the surface—and therefore it is a kinetic energy induced reaction. The process provides high quality and mechanically stable surface modification. This method has the disadvantage of excessive length of the whole process of surface preparation, up to a couple of hours, and small efficiency of the transfer into the vacuum that results in high consumption of protein solution. Furthermore, to perform this process, it is necessary to design a special apparatus into which the surface to be modified is inserted. The apparatus is then evacuated and the vacuum has to be maintained during the whole time of the modification process. After the vacuum is reached, the hyperthermal ions are collision-landed onto the surface for approximately three hours. Thus, only a few samples a day can be prepared in the apparatus and the cost of one surface modification reflects that.

In PCT/CZ2011/000118 (WO/2012/079549); and Krasny et al. J Mass Spectrom 2012 October; 47(10):1294-302, a method for surface modification of substrates for determination of phosphopeptides by desorption-ionization mass spectrometry is described. The surface of the substrate is modified by the solution of organometallic compounds (organic propoxides) of the elements of group 4B, namely Ti, Zr, and Hf, by electrospraying. Organic propoxides are thermally decomposed and a chemical reaction proceeds, during which an appropriate propoxide transforms into an oxide that binds onto the surface. In this document, an inorganic surface is used to detect the analytes-phosphopeptides, i.e. structural elements of phosphorylated proteins. Decomposition reaction of proteins is undesirable, because it would lead to lost of their biological activity.

The overview documents (Jaworek et al. J Mater Sci (2007) 42:266-297 and Morozov Adv. Biochem Eng. Biotechnol. 2010, 119: 115-1620) describe electrospray droplets depositions where charged droplets or microdroplets impact on surfaces. However, these techniques cannot be used for modification of hard surfaces, such as metal surface. Furthermore, the electrospray deposition of proteins from charged droplets does not form stable enough protein layer on the surface. Thus, it requires further treatment, for example fixation with 70% solution of glutaraldehyde (Lee et al. Biomaterials 24 (2003) 2045-2051). Adjuvants, for example disaccharides, can be added to maintain the proteins' activity during their electrospray deposition (Morozov Anal. Chem., 1999, 71 (7), pp 1415-1420).

SUMMARY OF THE INVENTION

The object of the present invention is to overcome the disadvantages of the prior art and to provide a modification method for a surface used as a substrate for analyte preconcentration in desorption-ionization mass spectrometry techniques and immunochemical assays. It is based on direct bonding of a protein onto a substrate surface. The subject-matter of the method according to the invention is introducing the carrier gas and the stock solution of the protein to be sprayed into an enclosed compartment that is under voltage [±(200-8000) V] and the pressure of 0.05 to 0.5 MPa, wherein the obtained charged aerosol exiting from the electrospray is introduced into the evaporation compartment 10 with the temperature in the range of 30 to 80° C., and the exiting dried aerosol is directed onto the surface 12 for modification, which is located behind the evaporation compartment 10.

According to the preferred embodiment of the invention, the surface 12 for modification is conductive, having the resistivity of the dry material lower than $10^{20}$ Ω·m and is under voltage [±(200-5000) V] of the polarity opposite to the voltage on the electrospray.

According to another preferred embodiment of the invention, the mask 13, that is under voltage [±(200-5000) V] of the polarity opposite to the voltage on the electrospray, is placed between the evaporation compartment 10 and the surface 12 for modification, in the distance of up to 3 mm from the surface 12 for modification.

According to another preferred embodiment of the invention, the carrier gas is preheated to a temperature of 30 to 80° C., preferably 30 to 40° C. before entering the enclosed compartment. The presented method of the modification of a substrate surface, where a direct bond is formed between the protein and the surface under the atmospheric pressure, overcomes the disadvantages of prior art, where the direct modification of substrate surface could have been reached only in vacuum or with the use of an interlayer. The modified surface of the substrate does not comprise any interlayer on which a nonspecific bond between the surface and other compounds in the sample could form. It is only the analyte that is specific for the partner protein, which can form the bond and selectively pre-concentrate on the surface. Versatility is another advantage of the method of modification according to the invention. As presented in the examples, structurally and chemically diverse proteins can be electrosprayed and consequently, after their landing, bound onto the surface. It is thus possible to prepare many types of surfaces for a wide variety of analytes within a few minutes.

The object of this invention is the modification method of surfaces that are used both as sample substrates at desorption-ionization mass spectrometry methods and as substrates for detection of compounds by immunoassays. The modification is achieved by deposition of proteins. This deposition process forms a biochemically active surface that consequently serves either for efficient separation of analyte from a sampled mixture sample, based on affinity interaction between the protein on the surface and its ligand in the sample to be detected, or if the deposited protein is an enzyme—for initiation of enzymatically catalysed reaction causing the analyte modification (for example proteolysis). The modification of the surface of the sample is achieved by electrospraying of protein solutions under the atmospheric pressure in the presence of carrier gas, which can be any inert gas. Preferably the carrier gas is selected from the group comprising nitrous oxide, nitrogen, helium, neon, argon, krypton, xenon, carbon dioxide. Aerosol formed by the spraying is nebulized by this carrier gas and dried by passing through the evaporation compartment to form desolvated protein ions that are consequently, due to the high voltage, driven onto the surface to be modified. Surprisingly, this modification is a results of a bond formed by desolvated protein ion on the surface. The modification is due to the fact that the desolvated ion, free of the solvation shell of a solvent, can react with the surface at the given temperature. This modification would not be possible under normal conditions in a solution. The electrical field of suitable polarity and intensity serves to direct and accelerate the ion towards the surface. After discharging its charge, the protein remains in native non-denaturated state and still exhibits biological activity.

It is possible to modify any solid surface with at least minimum conductivity up to the resistivity of about $10^{20}$ Ω·m. The surfaces used for modification can be any thermally stable metal, preferably selected from the group comprising stainless steel, gold, aluminium, also glass, thermally and mechanically stable synthetic polymer, a layer of silica nanostructures can be used too. Preferably the silica surfaces used in DIOS (Desorption/Ionization On Silicon) and NIMS (Nano structure-Initiator Mass Spectrometry) processes can be used, as well as the surfaces made from carbon nanotubes, graphene, etc. The microstructure of deposited protein is monitored by electron microscopy (FIGS. 3A to 3D).

Uncontested advantages of the method are that the surface modification is performed under atmospheric pressure and at the room temperature. Electrosprayed droplets are heated during their passage through the evaporation compartment, possibly also with preheated stream of the carrier gas. The heating leads to evaporation of a solvent and forming desolvated charged ions. The evaporation compartment is preferably heated to the temperature from 30° C. to 80° C., more preferably from 50° C. to 80° C. The ions can be focused more efficiently towards the surface with the use of high electric potential from an external source of the polarity opposite to of the obtained ions, which is placed at the surface for the modification or at the mask, which is placed no more than 3 mm in front of the surface. A mechanically stable layer of proteins bound to the surface is obtained; this layer is suitable for the purpose of selective analysis with the aid of affinity reaction and it is stable also after washing with aqueous buffers.

The method according to the invention is based on electrospray deposition of dry ions. It does not need any vacuum apparatus and the desolvation is not performed by transferring into the vacuum but under the atmospheric pressure by thermal drying (i.e. quick heating of droplets-desolvation) of electrosprayed aerosol in a specially preheated evaporating compartment. Thus, dried ions land on the surface for the modification. This method differs from the procedure of the above mentioned method by Volny M. et al, both in the mechanism of the surface modification and in the technical realization.

In contrast to the electrospray deposition of chemically modified (decomposed) organic propoxides, as disclosed in the patent document WO/2012/079549, in the present method of the invention, the protein molecules, such as enzymes, lectins, and antibodies, are deposited onto the substrate surface and they remain stable and still show biological activity after their binding on the surface. Another difference is that the surface is modified by proteins and that the analyte is always an appropriate affinity partner of a given protein. The process of electrospraying is also performed under different conditions (voltage, flow rate of the protein liquid, heating temperature, elevated temperature of the carrier gas due to its optional preheating, exposition time). The difference in the construction is the capillary configuration and the use of microspray with the microspray needle of the diameter in the range of 1-100 μm.

For the surface modification, the apparatus (FIG. 1) was used, consisting of an electrospray part, an evaporation compartment, and a terminal part comprising the surface for modification. The electrospray part comprises a T-splitter attached to a syringe pump. The syringe pump develops a pressure on the piston of the syringe placed inside the pump; the syringe being filled with a stock solution of the sprayed protein of the concentration in the range of 0.01 to 100 μmol/L.

The term "stock solution" refers to an aqueous solution, the mixture of water and at least one organic solvent or organic solvents that do not cause precipitation, aggregation, disaggregation, or denaturation of the sprayed proteins, which are dissolved in the stock solution at concentrations in the range from 0.01 to 100 μmol/L. Preferably the organic solvent is methanol or acetonitrile or a mixture thereof. The content of organic solvent or mixture of solvents in the aqueous mixture is up to 80% v/v, preferably in the range of 1 to 50% v/v. A suitable aqueous solution or an organic-aqueous mixture can contain a buffer as the conjugated pair of acid (or base) of the concentration from 1 μM to 1M, where the anion is preferably selected from the group comprising $CO_3^{2-}$, $CH_3COO^-$, $HCOO^-$, $Cl^-$ and the cation is preferably selected from the group comprising $H^+$, $Na^+$, $K^+$, $NH_4^+$, triethanolamine, trimethylamine, triethylamine or pyridine.

The term "sprayed protein" refers to a high-molecular biopolymer of mass of $10^3$ to $10^6$ (molar mass of $10^3$ to $10^6$ g/mol (Da)) composed of aminoacids, or the protein complex soluble in the above mentioned stock solution. It shows a biological activity. The protein suitable for the surface modification is an antibody, enzyme, lectin, and soluble proteins.

The term "antibody" refers to a protein also called immunoglobulin that can specifically bond an antigen. The antibody according to the invention is chosen from the group comprising immunoglobulins of the classes of IgA, IgG, IgD, IgE, or IgM, preferably antileptin antibody or FGF 21 antibody (Fibroblast Growth Factor 21 antibody).

The term "enzyme" refers to a simple or conjugated protein with catalytic activity. The enzyme according to the invention is selected from the group comprising oxidoreductases, transferases, hydrolases, lyases, isomerases or ligases, preferably proteases, for example trypsin or pepsin.

The term "lectin" refers to a protein of nonimmune origin that can highly specifically recognize and bind saccharide units, both free or bound on glycopeptides or glycolipids. Lectin according to the invention is chosen from the group comprising concanavalin A, lectins from cereal germs or peanuts, ricin, or lentil lectin.

The pressure on the piston of the syringe leads to pumping of the solution into the capillary towards the splitter (common flow rate is 0.05 to 5 μL/min). The splitter is terminated with a microspraying needle (diameter in the range of 1-100 μm). Further, the splitter is connected to the carrier gas intake, wherein the pressure of its valve is in the range of 0.05 to 0.5 MPa. The feed of the carrier gas can be performed both at room temperature or preheated to temperatures up to 80° C. Preferably it is preheated to the temperature in the range of 30 to 40° C. A high voltage source [±(500-8000)V] is included in the electrospray unit and it is connected to any conductive point on the electro spray. The evaporation compartment can be externally preheated up to the temperature of 80° C., depending on protein thermostability to prevent its denaturation or loss of activity. The final part includes the surface for modification; the mask can be placed in front of the surface, earthed or connected to another high voltage power supply (from 0 to ±8000V). If the mask is not applied, the voltage can be connected directly to the surface for modification. The distance between the mask and the evaporation compartment is less than 20 mm and more than 1 mm from the surface for modification. If the mask is not applied, the distance between the surface and the entrance from the evaporation compartment is less than 50 mm.

The modification process proceeds as follows: the high voltage source is connected to the electrospraying part. The solution of protein (A), at the flow rate of 0.01 to 50 μL/min, is introduced to the stream of compressed carrier gas (0.05 to 0.5 MPa), the carrier gas being an inert gas, preferably nitrogen, argon, helium, or neon. Due to the high voltage (+200-4000V) and the stream of compressed carrier gas, the protein solution (A) is electronebulized from the spraying needle to form a charged aerosol (B). The aerosol is consequently introduced into the evaporation compartment, where it is dried.

The thereby activated aerosol transforms into the dry aerosol and consequently into the ion beam (C). Dry charged particles-ions (C) can be further focused with the use of high voltage (±200-4000V) of the polarity opposite to the voltage on the electrospray brought on the mask or directly on the surface itself, and they are bound to the modified surface due to the energy gained from rapid heating, forming a macroscopically homogenous imprint on the surface. The shape and size of the imprint is defined by the shape and size of the gaps in the mask. If the mask is not applied, the imprint size and shape is defined by the cross-section of the evaporation compartment. The modified surface can be used directly for the selective analysis by an immunochemical assay, or, after deposition of a ionization matrix, the samples can be analysed by desorption-ionization mass spectrometry, for example MALDI MS (Matrix-Assisted Laser Desorption Ionization Mass Spectrometry).

This method of surface modification by proteins provides high-quality surface, free of cracks or other macroscopic nonhomogenities, wherein the protein is bound directly onto the substrate, without the use of any interlayer (FIGS. 3A to 3D).

The modified surface was used for simplification of the analysis of biological samples, as shown in Examples 1 to 3.

BRIEF DESCRIPTION OF THE DRAWINGS

FIG. 1: The apparatus for the modification of surfaces for desorption-ionization mass spectrometry comprises a T-splitter 1, a syringe pump 2 actuating the piston 3 of the syringe 4 with the stock solution A, a tube 5, a microspraying needle 6 on the splitter 1, the intake of the carrier gas 7 with the possibility of preheating, a high voltage power supply 8 for the electrospray connected to the conductive part 9 of the syringe 4, the evaporating compartment 10, the surface 12 for modification, and the mask 13, a high voltage power supply 11 connected to the mask 13 and the surface 12 for modification. When the stock solution passes the sprayer, the charged aerosol (B) forms and transforms into a dried aerosol/ion beam (C) when passing the optionally heated tube.

FIG. 2: The apparatus for modification of surfaces for desorption-ionization mass spectrometry comprises a T-splitter 1, a syringe pump 2 actuating the piston 3 of the syringe 4 with the stock solution A, a tube 5, a microspraying needle 6 on the splitter 1, the intake of the carrier gas 7 with the possibility of preheating, a high voltage power supply 8 for the electrospray connected to the conductive part 9 of the syringe 4, the evaporating compartment 10, the surface for modification, a high voltage power supply 11 connected to the surface 12 for modification. When the stock solution passes the sprayer, the charged aerosol (B) forms and transforms into a dried aerosol/ion beam (C).

FIGS. 3A to 3D: The images of modified surfaces obtained by electron microscopy. The upper panel of the pictures shows microscopic comparison of a protein deposed on stainless steel before (A) and after washing (B) (see FIG. 3A). The image from an electron microscope documents the removal of the protein layer not bound on the surface. The middle panel of the pictures shows comparison of the surfaces with a protein deposited on stainless steel after washing (C) and the stainless steel surface without the deposited protein (D) (see FIG. 3B). The images E and F (see FIG. 3C) show microscopic comparison of the glass surface before and after washing. The bottom panels in the figure show microscopic comparison of the protein deposited and bound on the glass after washing (G) and of the intact glass surface without the deposited protein (H) (see FIG. 3D).

FIGS. 4A and 4B: A) The mass spectrum of peptides from human haptoglobin incubated for 2 hours on the trypsin deposited surface at 37° C. The detected peptides are emphasized with black-underlined italic and they cover 46% of the total sequence (see FIG. 4A). B) The mass spectrum of peptides from myoglobin incubated for 20 minutes on the trypsin deposited surface at 37° C. (see FIG. 4B). The detected peptides are emphasized with black-underlined italic and they cover 78% of the total sequence. The identification was done by using the MASCOT search program (Matrix Science) with SwissProt database.

FIGS. 5A and 5B: The mass spectrum of tryptic peptides of β N-acetylhexosaminidase after enrichment (the black spectrum) on the surface with deposited lectin concanavalin A and before the enrichment (the grey spectrum). Concanavalin A selectively interacts with O-glycosidically bound glycans that contain mannoses (A) (see FIG. 5A) and with N-glycosidically bound glycans referred to as high-mannose-type (B) (see FIG. 5B). The mass spectrum A shows the enrichment of the glycopeptide WVPAATEAPISSFEPFPTPTAGAS (pep) and of its truncated form WVPAATEAPISSFEPFPTPTAGA (pep*) containing up to 6 mannoses. The mass spectrum B represents the enrichment of the glycopeptide ELSDIFPDHWFHVGGDEIQPNCFNFSTHVTK containing high-mannose glycans (the grey square represents N-acetylglucosamine, the grey circle represents mannose).

FIG. 6: The mass spectrum of tryptic peptides from the mixture of immunoglobulins IgG1 and IgG2 after enrichment (the black spectrum) on the surface with deposited lectin from wheat germs (wheat germ agglutinin) and before enrichment (the grey spectrum). The wheat germ lectin selectively enriches the glycopeptides containing terminal saccharide N-acetylglucosamine. In the spectrum, there are two enriched glycopeptides denoted as pep.1 (TKPREEQFNSTFR-IgG2) and pep.2 (TKPREEQYNSTYR-IgG1) that contain different glycan structures (the grey square represents N-acetylglucosamine, the grey circle represents mannose, grey triangle represents fructose, and the black circle represents galactose).

FIG. 7: A) The mass spectrum of standard protein FGF-21 (Fibroblast Growth Factor 21) after its incubation with polyclonal antibody against human FGF-21, which was deposited on the surface (the black spectrum). The signal intensity of the protein shows that even after careful washing of the surface the FGF-21 protein remains bound on the antibody. The grey spectrum shows the standard protein FGF-21 of the same amount (1 pmol). B) The UV/VIS spectrum of the immunoenzymatic reaction measured after antigen FGF-21 incubation in artificial serum with polyclonal antibody in comparison with human FGF-21 deposited on the surface. At the wavelength of 450 nm, significant increase of absorbance occurs on the surface with the bound antigen (the black spectrum) compare to the surface without FGF-21 antigen (the grey spectrum). The inset figure shows photons detected by CCD (Charge-Coupled Device) camera after immunoenzymatic reaction employing chemiluminescence that proceeded directly on the surface modified with the antibody against human FGF-21 (Fibroblast Growth Factor 21). C) The mass spectrum of a standard protein leptin after incubation with a polyclonal antibody in comparison with human leptin that was deposited on the surface (the black spectrum). The leptin remains bound on the antibody after washing. The grey spectrum shows the same amount (1 pmol) of the deposited standard leptin protein D) The mass spectrum of leptin deposited in the presence of artificial serum on the surface modified with polyclonal antibody in comparison with human leptin (black spectrum). After washing the surface, the leptin enrichment occurs, which can be identified in the spectrum. The grey spectrum represents leptin in artificial serum deposited on the surface that was not modified with an antibody.

Figure 8:
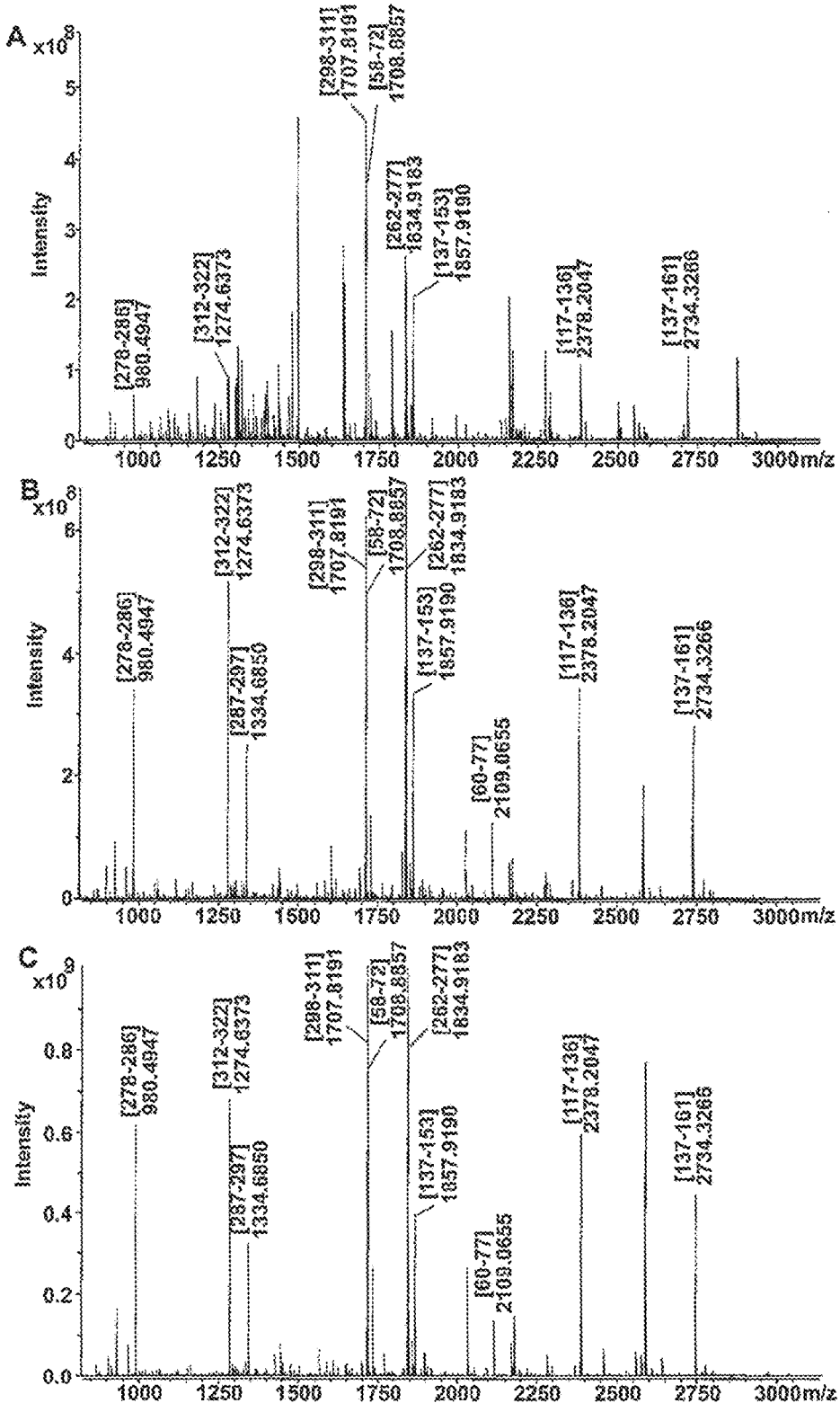

FIG. 8: The mass spectra of haptoglobin molecule tryptic peptides after digestion on the surface prepared by tryspin deposition at different concentrations: A) 0.01 µmol/L B) 1 µmol/L, and C) 100 µmol/L FIG. 9: The mass spectra of haptoglobin molecule tryptic peptides after digestion on the surface prepared by deposition of trypsin in buffer (ammonium bicarbonate) at different concentrations: A) 1 µmol/L, B) 1 mmol/L, and C) 1 mol/L.

Figure 10:
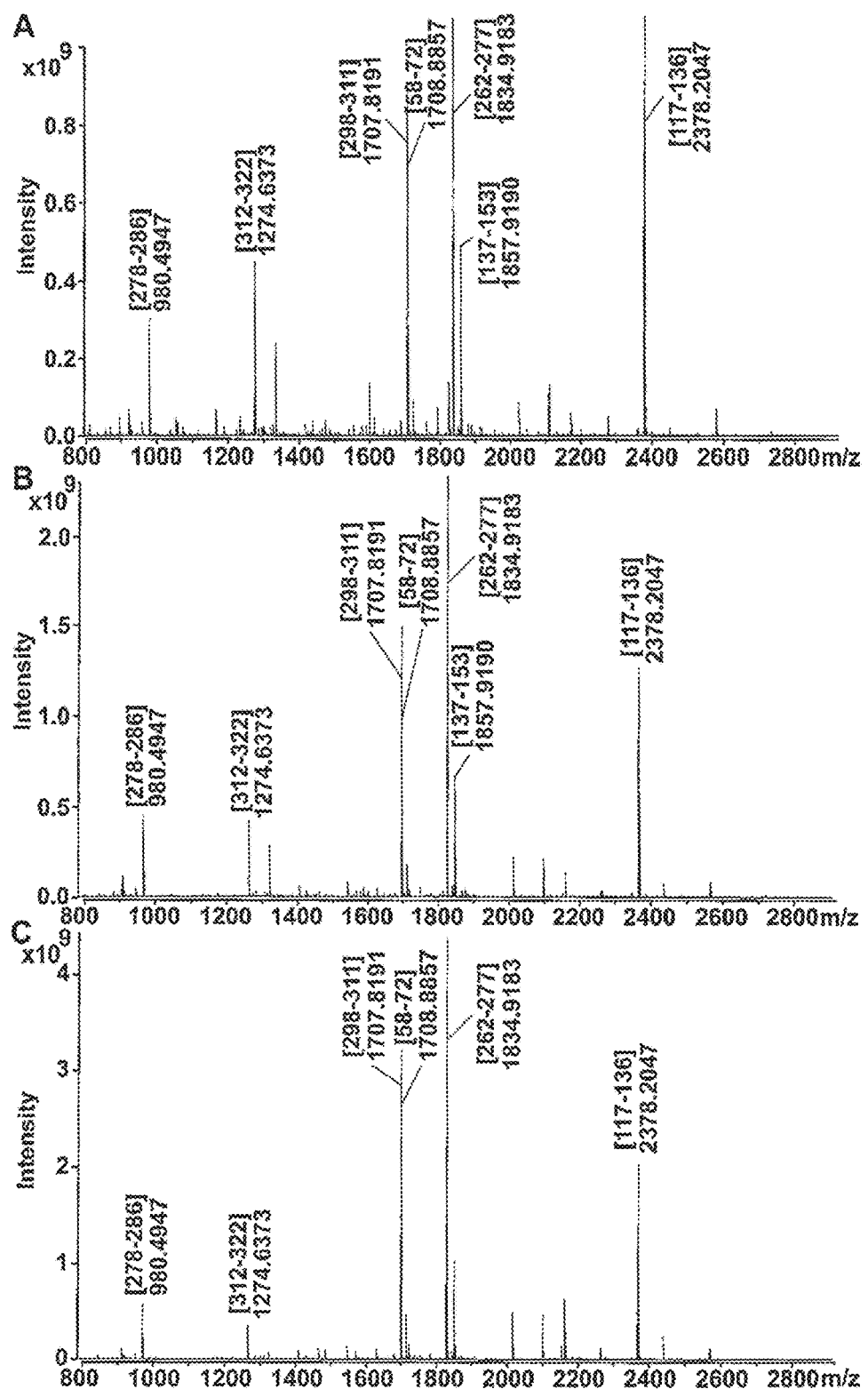

FIG. 10: The mass spectra of haptoglobin molecule tryptic peptides after digestion on the surface prepared by trypsin deposition in the presence of an organic solvent (acetonitrile) at different concentrations: A) 0% v/v, B) 40% v/v, and C) 80% v/v.

Figure 11:
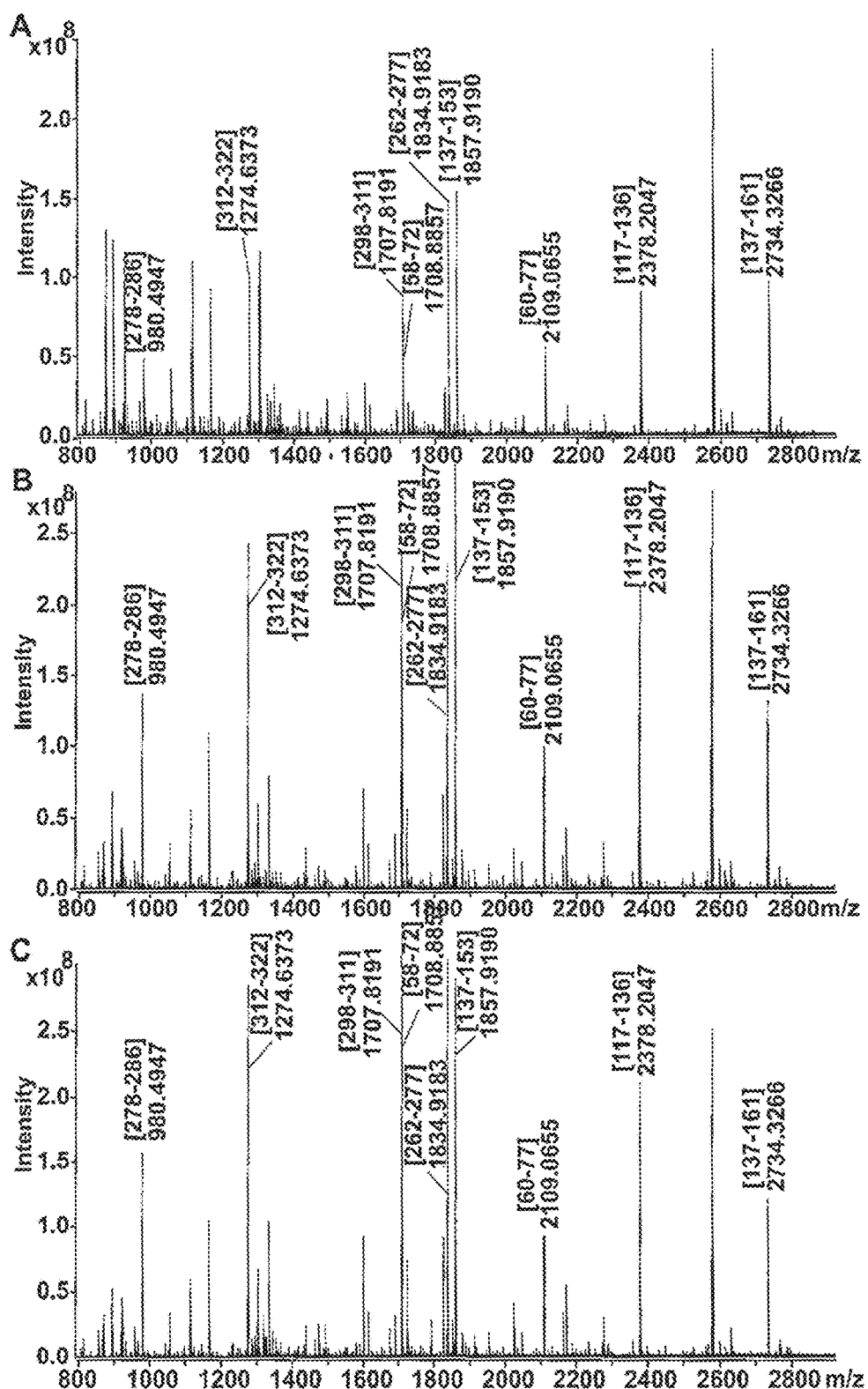

FIG. 11: The mass spectra of tryptic peptides of the haptoglobin molecule after digestion on the surface prepared by trypsin deposition at different temperatures of the desolvation compartment: A) 30° C., B) 50° C., and C) 80° C.

PREFERRED EMBODIMENTS OF THE INVENTION

Example 1 (Enzyme: Trypsin 23.3 kDa, Pepsin 34.6 kDa)

The modified surface was prepared by performing the electrospray deposition and dry ions landing on the surface for 60 minutes according to the following procedure:

The values of the apparatus from FIG. 1 were set as follows:

Flow rate of the pump 2: 2 µL/min
Power supply 8 voltage brought to the conductive part 9 of the syringe 4: 1500V
Temperature of the tube shaped evaporation compartment 10: 80° C.
Power supply 11 voltage on the mask 13: −1500V
Pressure of the carrier gas inflow 7: 0.25 MPa
Carrier gas type: nitrogen
Carrier gas temperature: room temperature (21° C.)
Shape of the gap in the mask: circle; diameter=2 mm The syringe pump 2 was filled with trypsin solution of the molar mass 23 300 Da (or pepsin, molar mass of 34 600 Da) at the concentration of 2 µmol/L in 5 mmol/L ammonium acetate, 30% v/v. acetonitrile (solution A). The high voltage power supply 8 was connected to the conductive part 9 of the syringe 4 with the stock solution; the syringe was connected via the capillar tube 5 with the splitter 1. The trypsin (or pepsin) solution (A) was introduced into the splitter with the use of the syringe pump 2, where it was electronebulized, due to the high voltage and the inflow stream of the compressed carrier gas, from the spray needle to form the charged aerosol (B). The formed aerosol was introduced to the 5 mm diameter tube-shaped compartment 10, where the aerosol was dried and then it further passed the mask 13 to the aluminium surface 12. After completing the process, the high voltage from both the power supplies 8 and 11 was turned off; the surface was removed and washed with water. 240 pmol of trypsin (pepsin) was used for the surface modification by this method and the formed layer had circle shape with the diameter given by the mask (2 mm). This layer was stable both for sample preparation and its analysis.

Figure 4A:
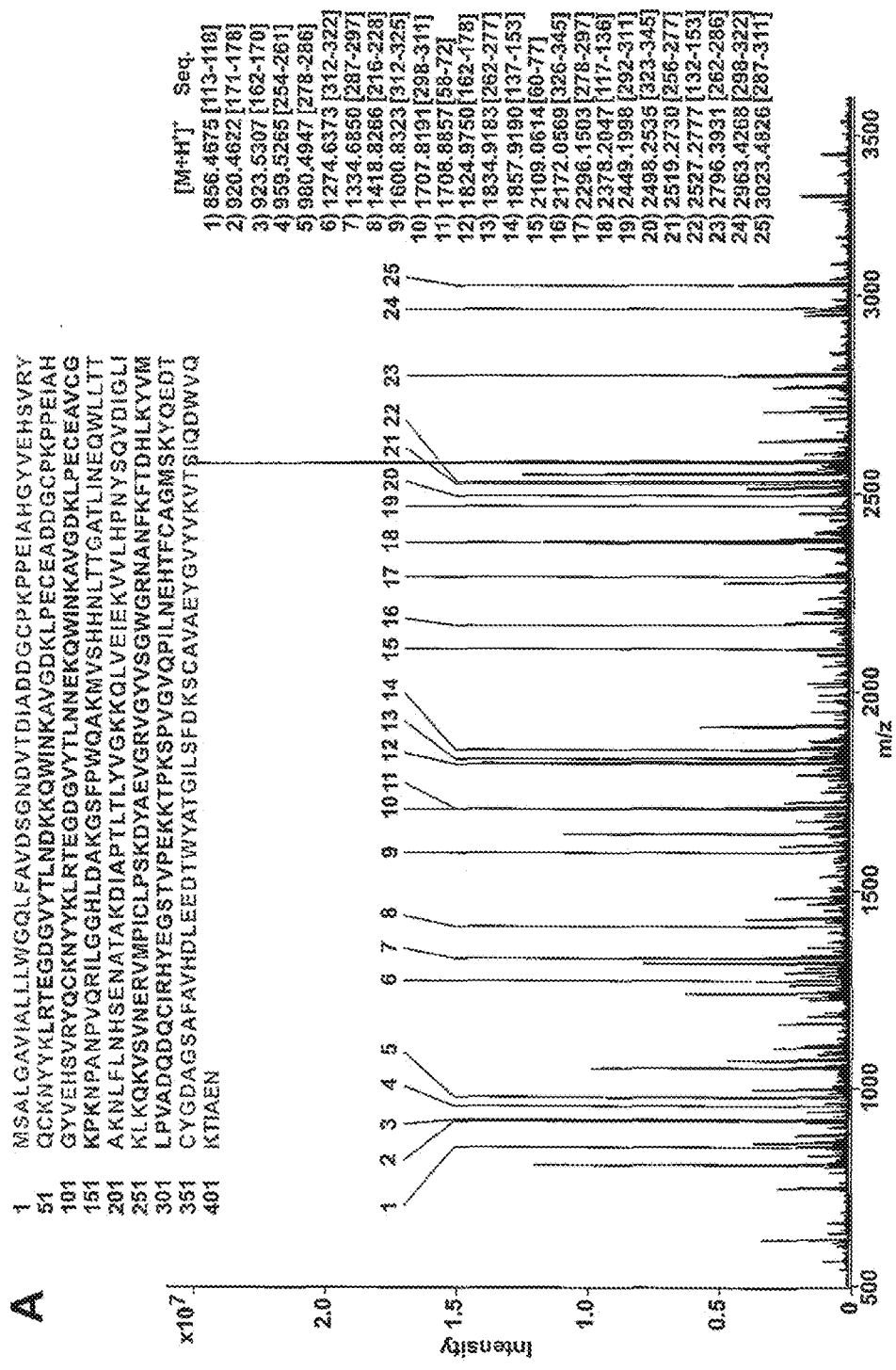
Figure 4B:
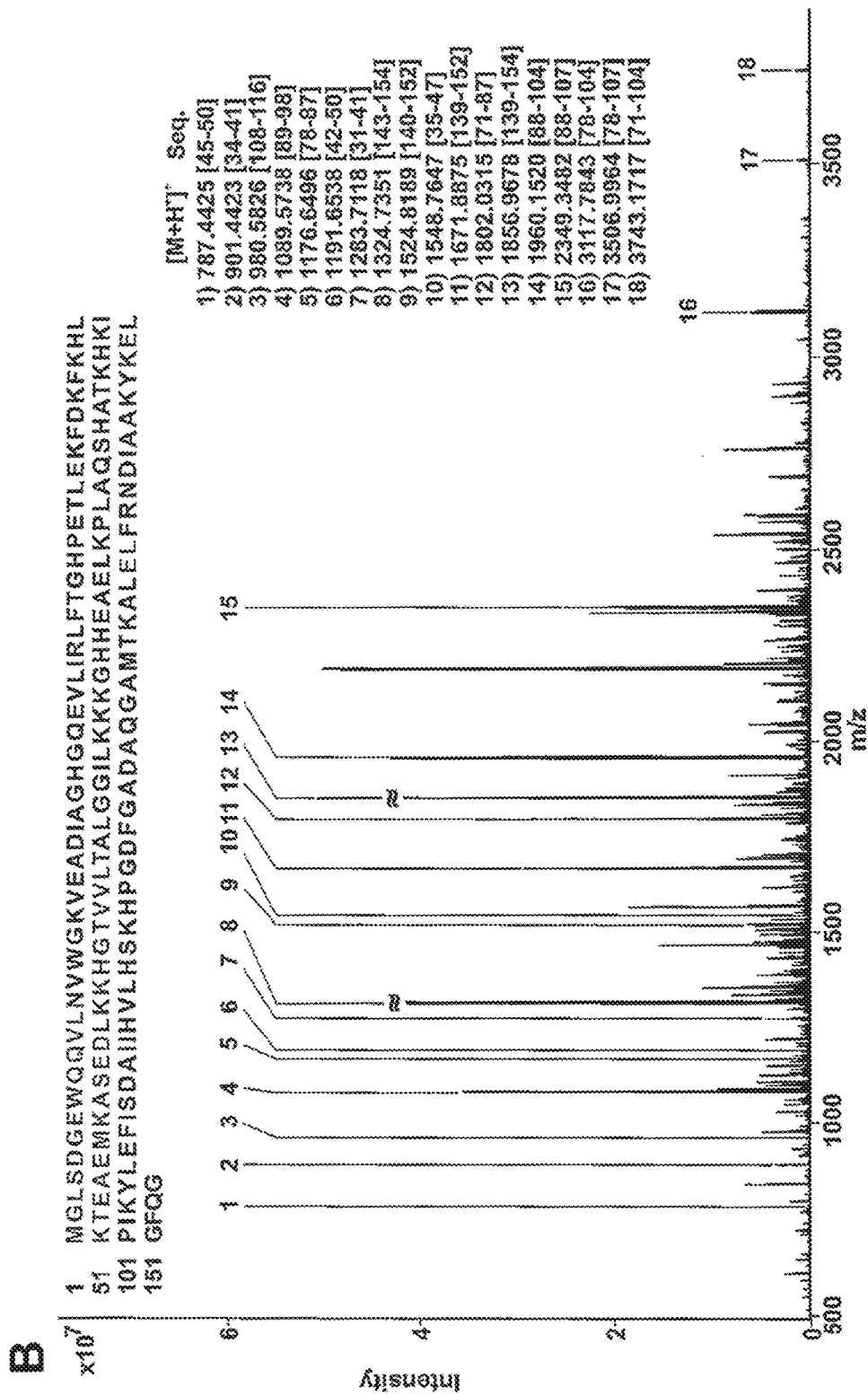

1 µL of 50 mM solution of ammonium bicarbonate, pH 7.9, with dissolved haptoglobin, at the concentration of 1 pmol/µl, was sampled onto the surface with trypsin. The solution of myoglobin in 50 mM glycine buffer, pH 2.3, was sampled onto the surface with pepsin. The surfaces with deposited haptoglobin and myoglogin were placed into a Petri dish and incubated for 2 hours (haptoglobin) and 20 minutes (myoglobin) at 37° C. Haptoglobin and myoglobin molecules were digestioned into particular peptides due to the enzyme activity of both modified surfaces. The resulted peptides were immediately analysed from the surface, without any sample manipulation, by means of desorption-ionization mass spectrometry, specifically by the MALDI method. FIGS. 4A and 4B show the obtained spectra of the peptides. The exact individual peptide masses obtained from the spectra lead to identification of amino acids sequences of haptoglobin and myoglobin as it is also shown in FIGS. 4A and 4B.

The total sequence coverage of the determined sequences was 46% for haptoglobin and 78% for myoglobin, which is sufficient for the identification of haptoglobin in a protein database such as for example Swissprot or NCBI.

Other surfaces were trypsin modified according to the above described method, wherein the methods differed in one parameter only:

1) Trypsin concentration: A) 0.01 µmol/L, B) 1 µmol/L, and C) 100 µmol/L. The mass spectra of tryptic peptides of haptoglobin molecule after digestion on the modified surface are shown in FIG. 8.

Figure 9:
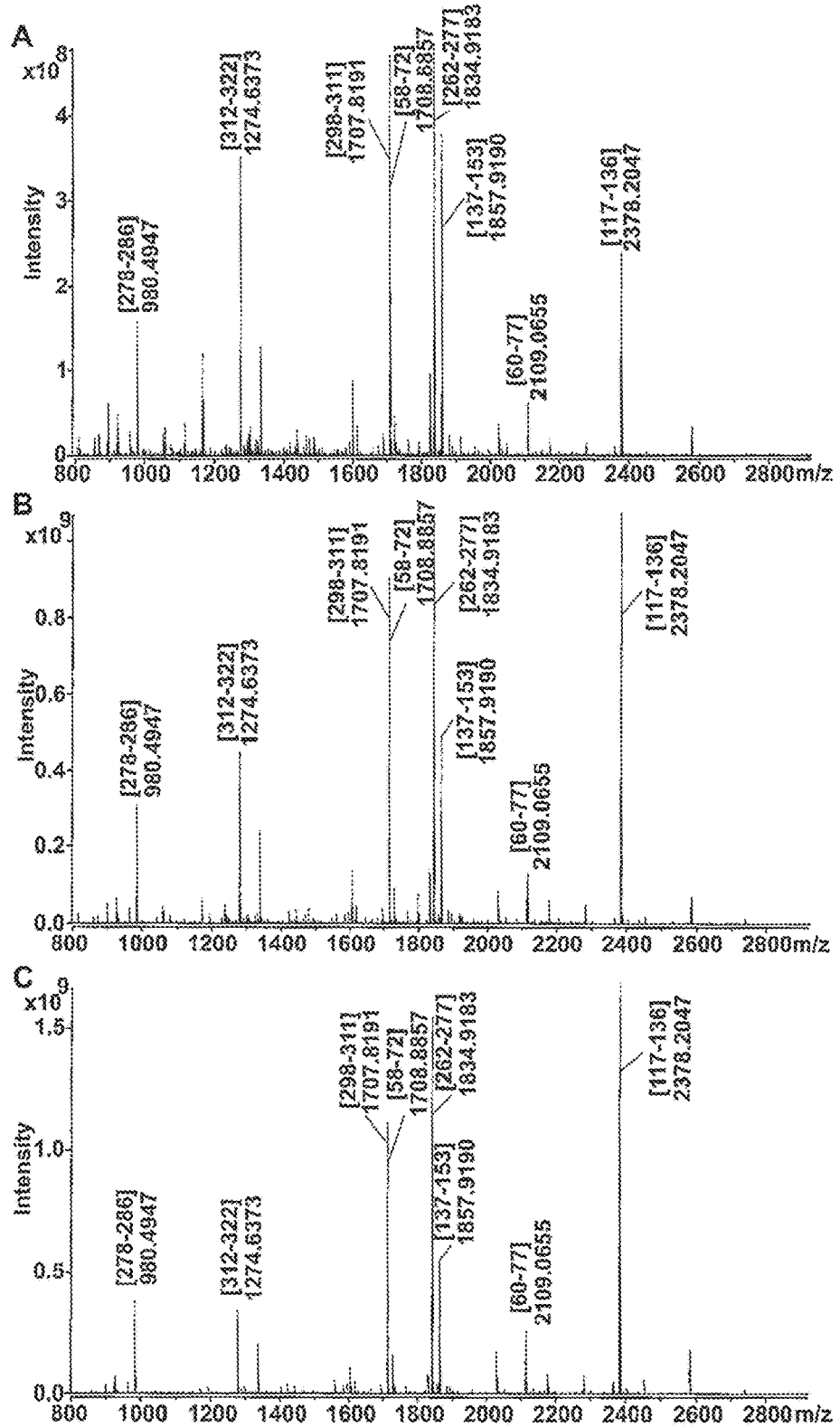

2) Buffer concentration (ammonium bicarbonate): A) 1 µmol/L, B) 1 mmol/L, and C) 1 mol/L. The mass spectra of tryptic peptides of haptoglobin molecule after digestion on the modified surface are shown in FIG. 9.

3) In an aqueous solution and in the presence of an organic solvent: A) 0% v/v, B) 40% v/v, and C) 80% v/v. The mass spectra of tryptic peptides of haptoglobin molecule after digestion on the modified surface are shown in FIG. 10.

4) The temperature of the evaporation compartment during the trypsin deposition: A) 30° C., B) 50° C. a C) 80° C. The mass spectra of tryptic peptides of haptoglobin molecule after digestion on the modified surface are shown in FIG. 11.

Example 2 (Lectin: Concanavalin A 25.5 kDa Monomer, 102 kDa Tetramer and Wheat Germ Lectin (Wheat Germ Agglutinin) 17.5 kDa Monomer, 35 kDa Dimer)

Figure 5A:
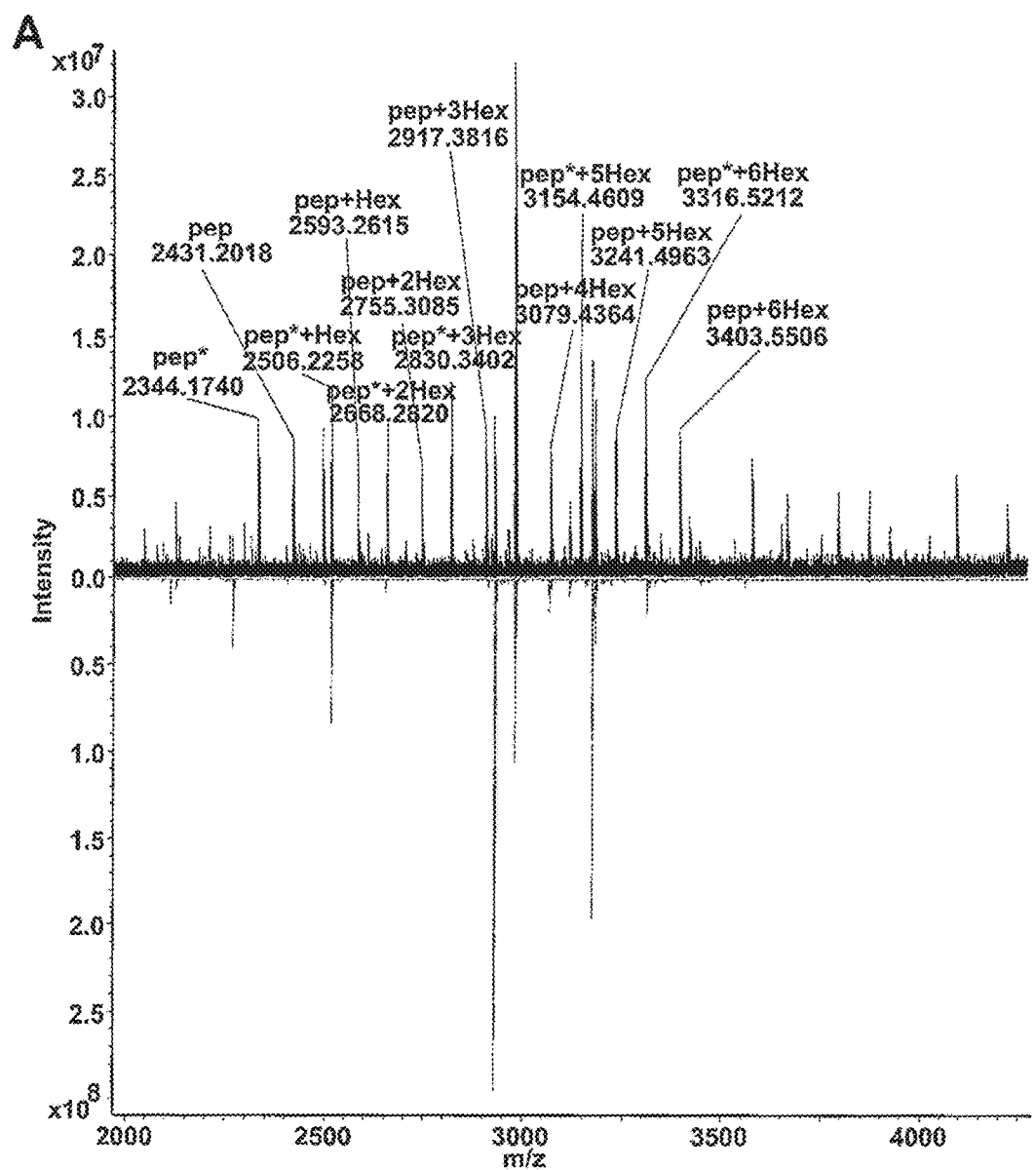
Figure 5B:
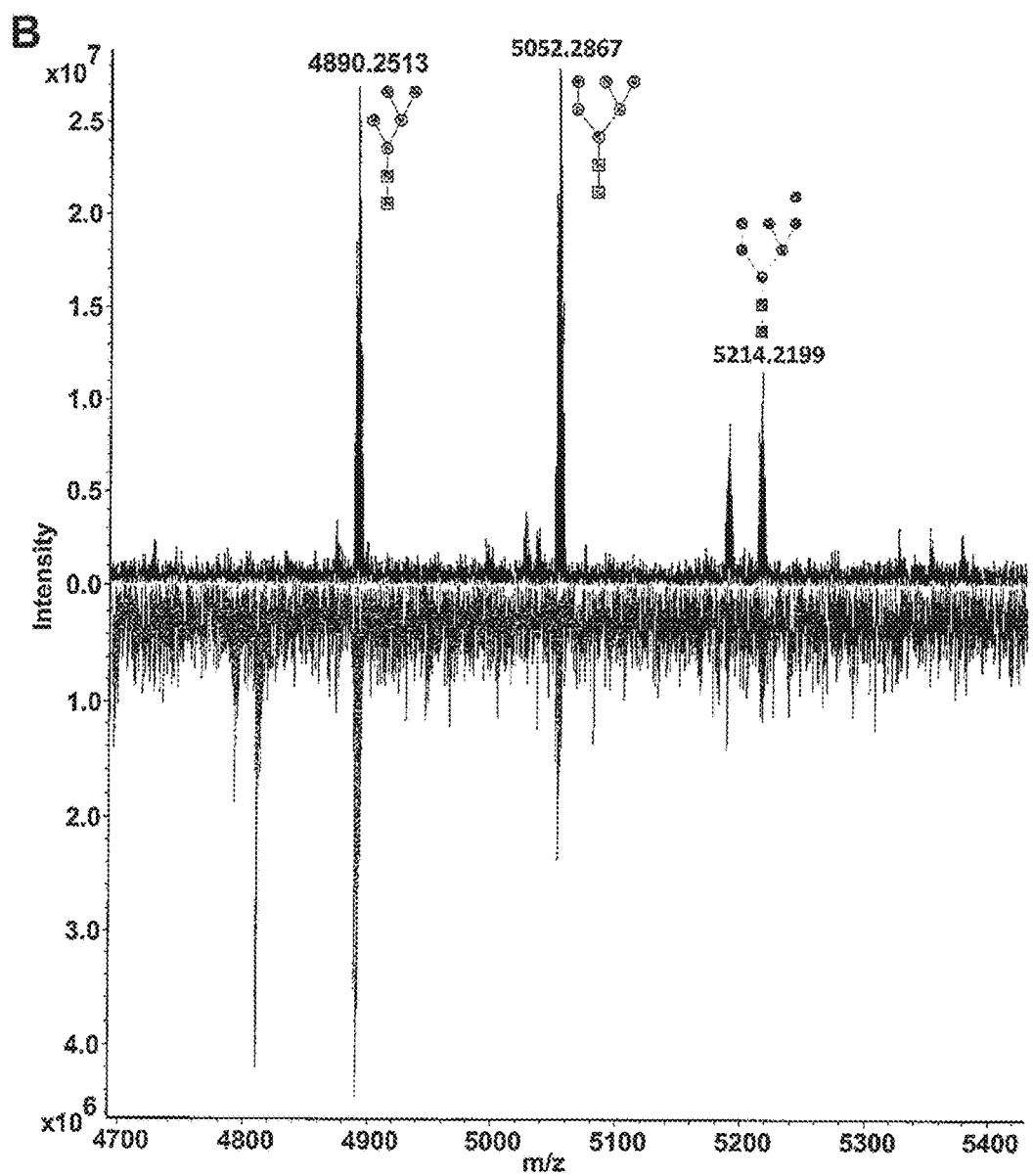
Figure 6:
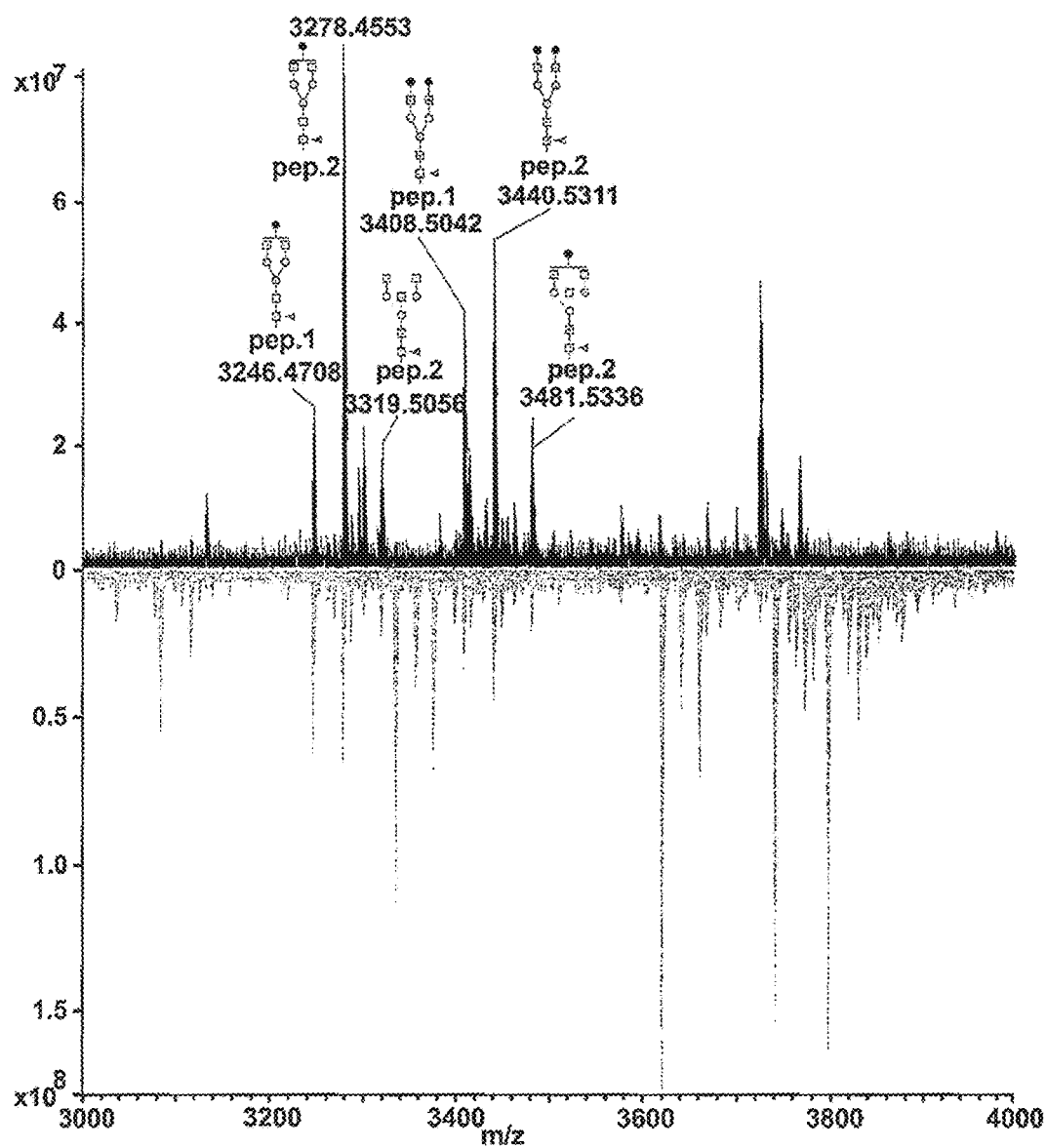

The modified surface was prepared by performing the electrospray deposition and landing of the dry ions on the surface for 12 minutes according to the following procedure:

The values of the apparatus from FIG. 1 were set as follows:

Flow rate of the syringe pump 2: 2 µL/min
Power supply 8 voltage brought to the spray needle 6: +1000V
Temperature of the tube shaped evaporation compartment 10: 55° C.
Power supply 11 voltage brought to the mask 13: −1000V
Pressure at the carrier gas intake 7: 0.25 MPa
Carrier gas type: nitrogen
Temperature of the carrier gas: 35° C.
Shape of the gap in the mask: circle; diameter=2 mm The syringe pump 2 was filled with concanavalin A solution (molar mass 25500 Da) or wheat germs lectin (molar mass 17500 Da) of the concentration of 10 μmol/L in 5 mM ammonium acetate solution, 30% v/v acetonitrile (alternatively in 50% v/v methanol) (Solution A) and connected with the splitter via the capillar tube 5. The high voltage power supply 8 was connected with the spray needle 6. The solution of concanavalin A or wheat germs lectin (A) was introduced into the splitter with the use of the syringe pump 2, where it was electronebulized due to the high voltage and the inflow stream of compressed carrier gas, from the spray needle to form the charged aerosol (B). The formed aerosol was introduced to the 5 mm diameter tube-shaped compartment evaporation compartment 10, where the aerosol was dried and then it further passed the mask 13 to the stainless steel surface for modification. After completing the process, both high voltage power supplies 8 and 11 were turned off, the surface was removed and washed with water. 120 pmol of concanavalin A or wheat germs lectin was used for the surface modification by this method and the formed layer had circular shape with the diameter defined by the mask (2 mm). This layer was stable both for sample preparation and its analysis. The solution of tryptic peptides of hexosaminidase (from *Aspergillus Oryzae*) or of the mixture of IgG1 and IgG2 (from human) of the volume of 1 μl and concentration 10 pmol/μl was sampled on the surface modified by this method. Due to the affinity interaction between concanavalin A or wheat germs lectin on the surface and glycopeptides, the glycopeptides were specifically bound. Other components of the sample were removed by washing the surface with PBS (Phosphate Buffered Saline) or TBS (Tris-buffered Saline). In addition, the sample can be deposited repeatedly on the modified surface, because due to removing the other components of the sample by washing, a higher amount of the analyte itself can be dosed. These effects are illustrated in FIGS. 5A, 5B and 6 that show the comparison of analysis by MALDI mass spectrometry from standard commercially available MALDI surface and from MALDI surface with bound concanavalin A or wheat germs lectin. By performing the analysis on the concanavalin surface, three forms of N-glycosidically bound high-mannose glycans were detected and few forms of O-glycosidically bound glycans were found. Using the analysis on the standard surface, only two N-glycosidically bound glycans and only few variants of O-glycopeptide were detected. In the case of deposited wheat germs lectin, two N-glycosylated peptides (one form IgG1 and one from IgG2) were enriched with complex saccharides.

Example 3 (Antibody: Anti FGF-21, Anti Leptin, 150 kDa)

The modified surface was prepared by performing the electrospray deposition and landing of the dry ions on the surface for 60 minutes according to the following procedure.

Figure 2:
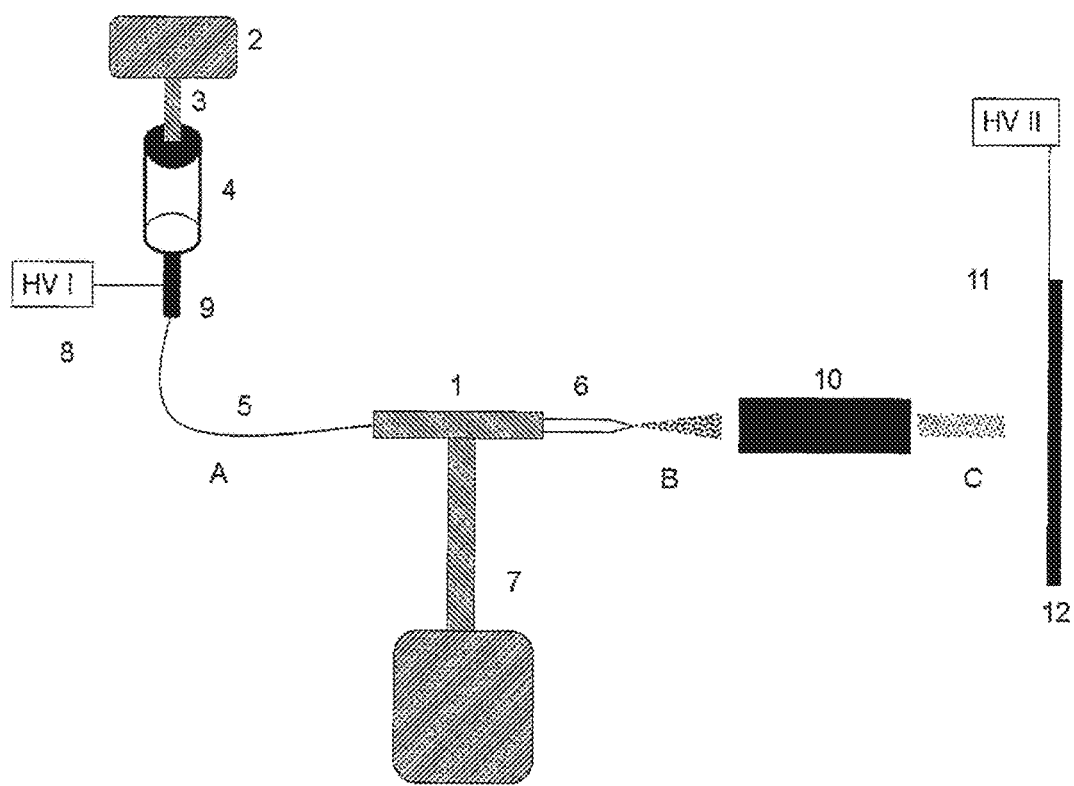
Figure 3A:
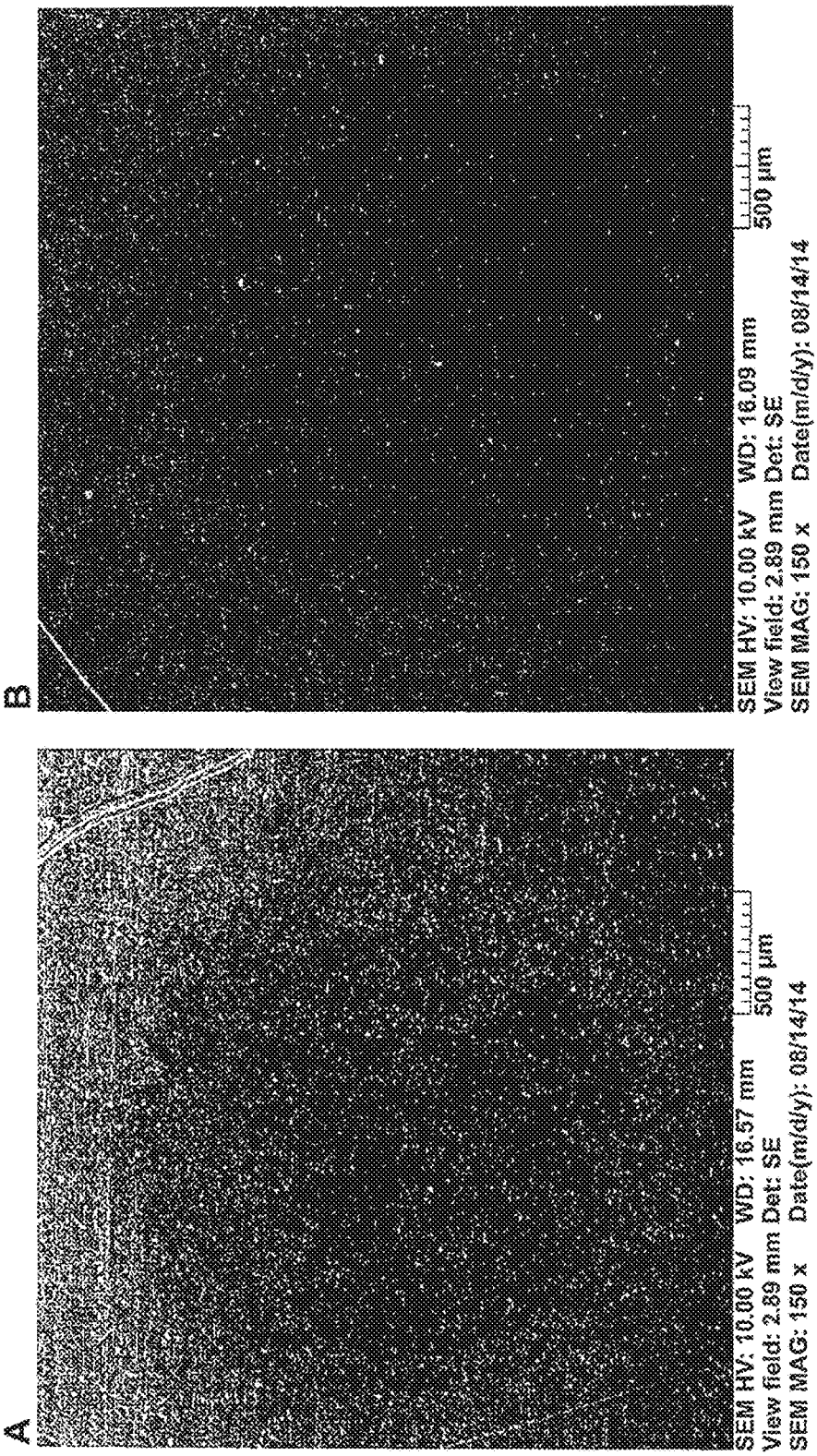
Figure 3B:
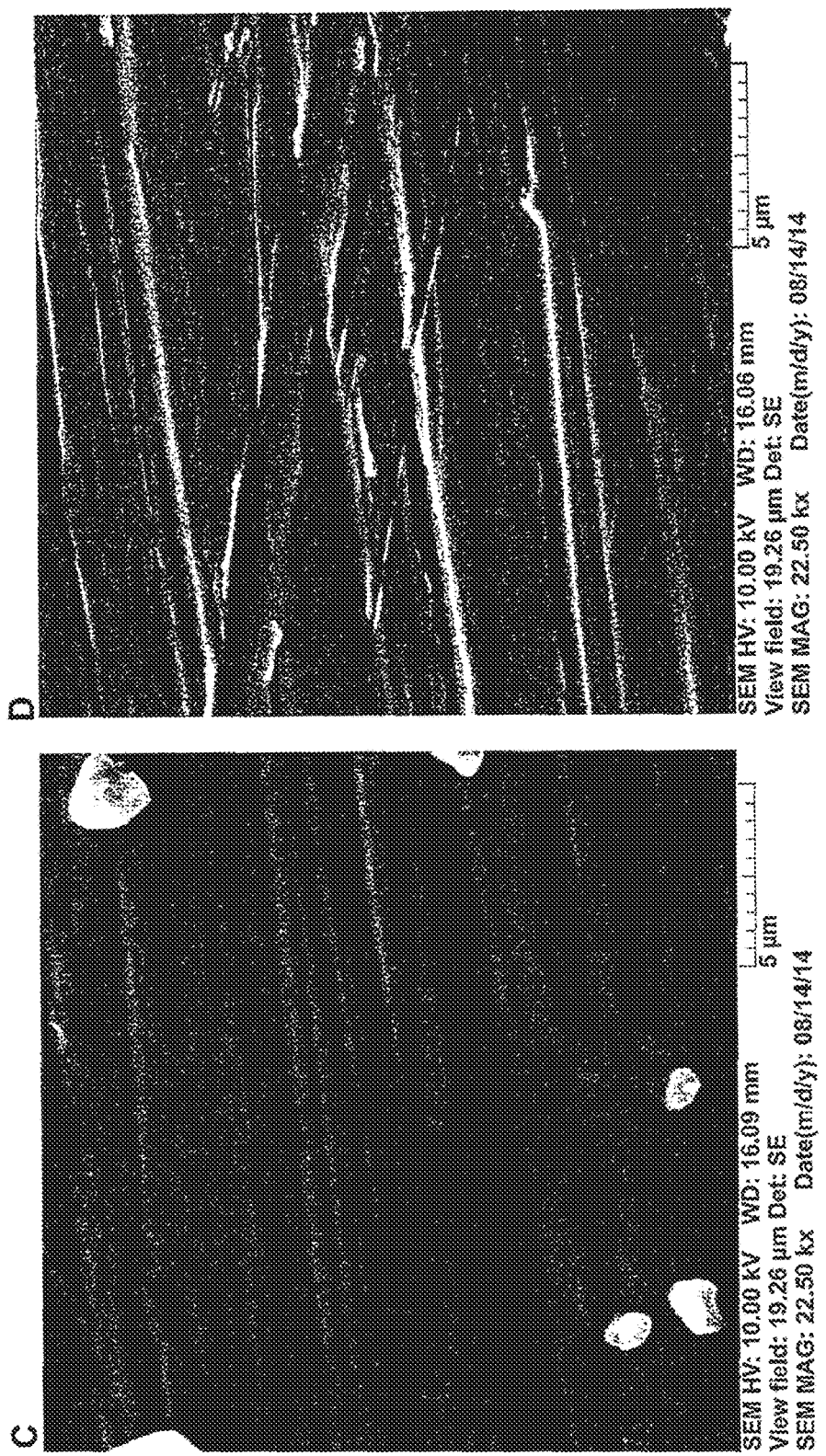
Figure 3D:
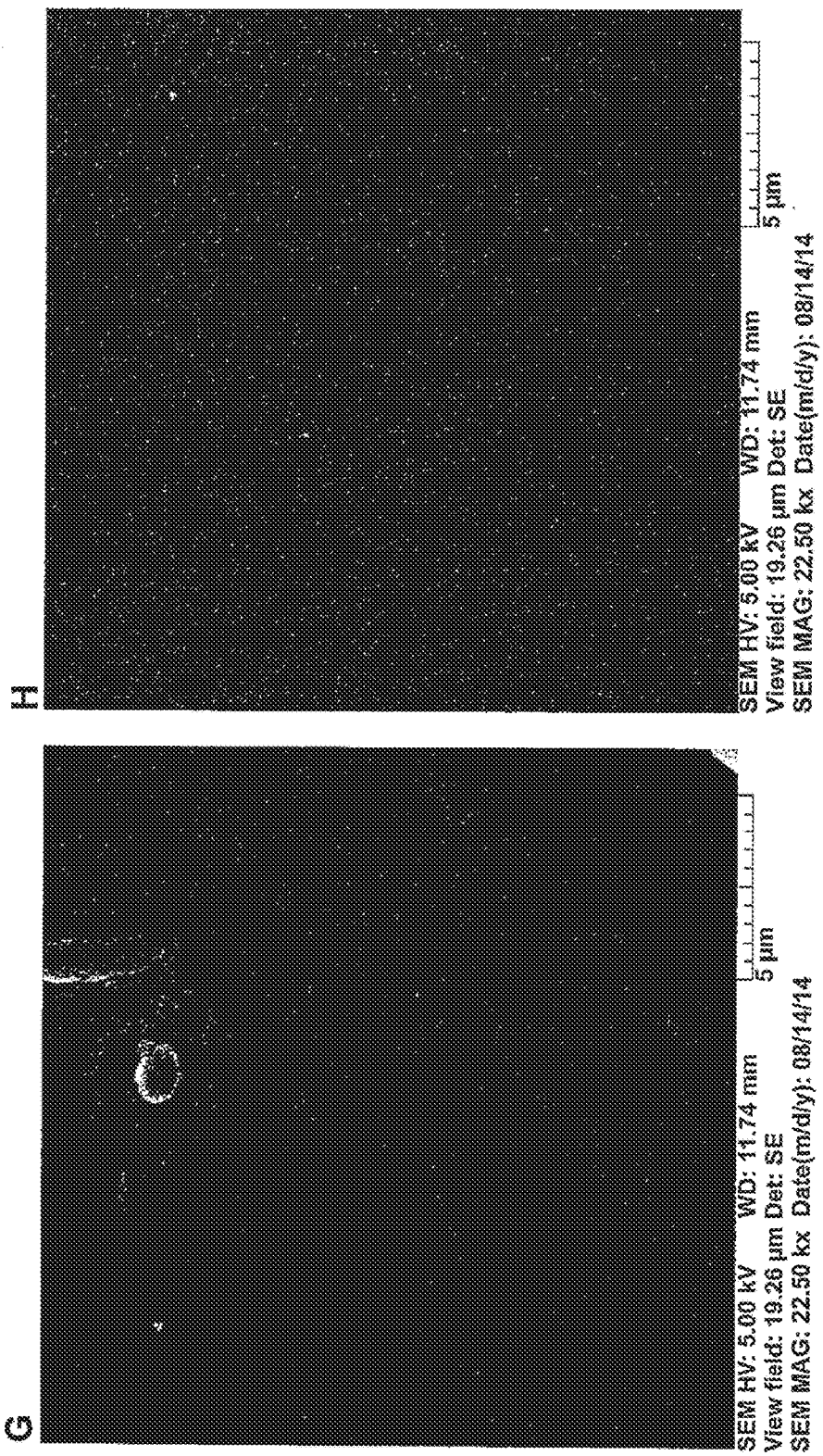

The values of the apparatus from FIG. 2 were set as follows:

Syringe pump 2 flow rate: 2 μL/min
Power supply 8 voltage brought to the conductive part 9 of the syringe: +1000V
Temperature of the tube shaped evaporation compartment 10: 45° C.
Power supply 11 voltage brought to the surface 12: −1000V
Pressure at the carrier gas intake 7: 0.25 MPa
Carrier gas temperature: 30° C.
Carrier gas: nitrogen
The syringe was filled with the solution of leptin specific polyclonal antibody (antileptin antibody), molar mass 150000 Da, and concentration 2 μmol/L in 5 mM ammonium acetate, 30% v/v. acetonitrile (Solution A). The syringe with the Solution A was inserted into the syringe pump 2. The high voltage power supply 8 was connected to the conductive part 9 of the syringe 4 with the stock solution and this was connected with the splitter 1 via the capillar tube 5. The antileptin antibody solution (A) was introduced to the splitter with the use of the syringe pump 2 where it was electronebulized due to the high voltage and the inflow stream of compressed carrier gas, from the spray needle to form the charged aerosol (B). The formed aerosol was introduced to the 5 mm diameter tube-shaped evaporation compartment 10, where the aerosol was dried and then it further passed to the aluminium surface. After completing the process, both high voltage power supplies 8 and 11 were turned off, the surface was removed and washed with water. The formed antibody layer had circular shape with the diameter given by the diameter of the evaporation compartment (2 mm) was formed by this method. This layer was stable both for sample preparation and its analysis. The same method was used also for the modification of the surface with polyclonal antibody against human FGF-21.

Figure 7:
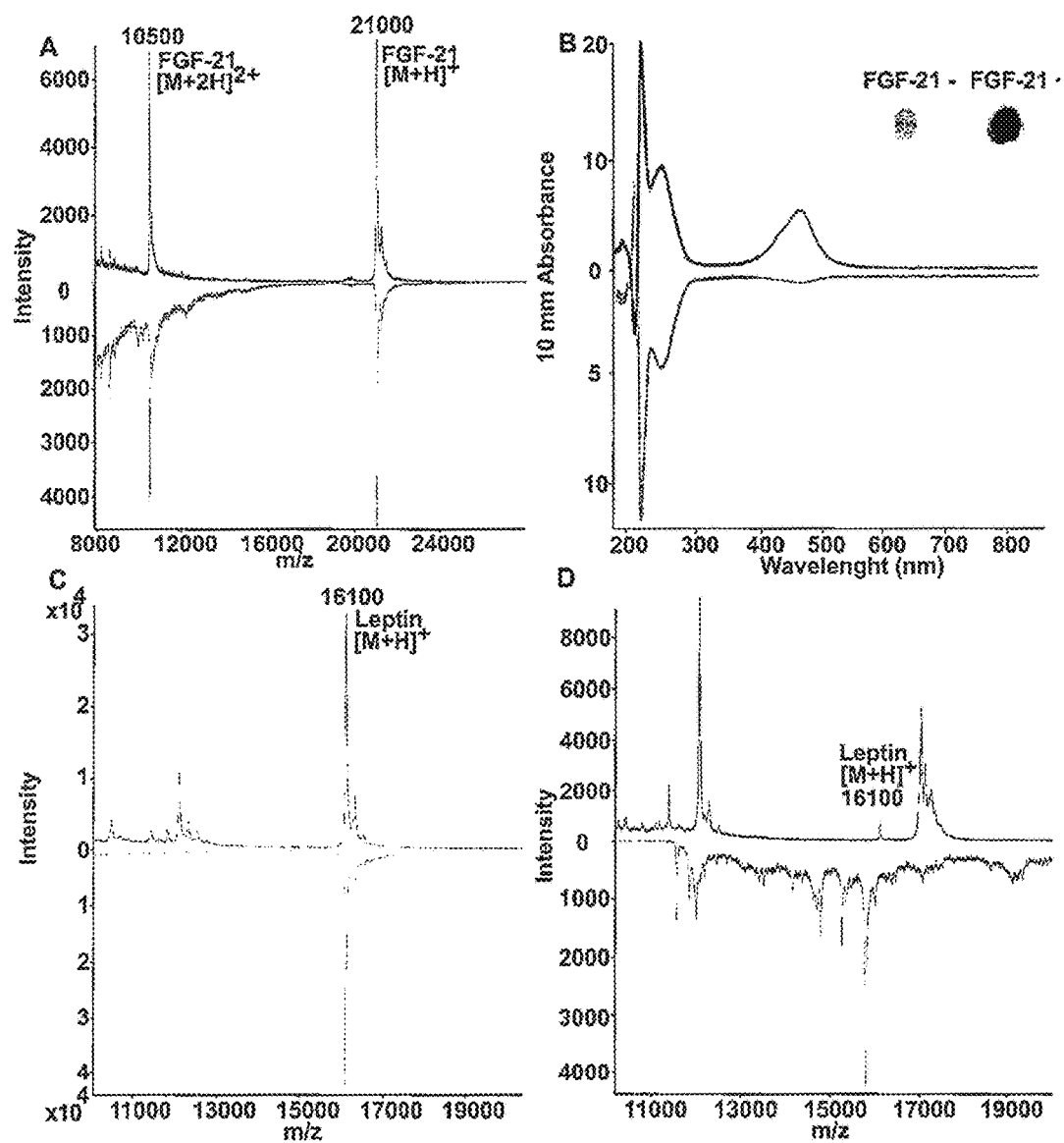

Standards of proteins leptin and FGF-21 and leptin and FGF-21 dissolved in an artificial serum were deposited onto the prepared surfaces. After application of solutions of the individual antigens, the surfaces were enclosed in Petri dishes to slow down the evaporation, and incubated for 1 hour. After washing the surfaces with PBS, mass spectrometry analysis of proteins (peptides, if digested antigen was sampled onto a modified surface) or immunoenzymatic assay was performed. FIG. 7 shows the comparison of the mass spectra of the proteins leptin and FGF-21 on the modified and standard surface. It is apparent from the spectra that even after a careful washing of the surfaces, the antigens remain bound on the respective antibodies. Immunoenzymatic assay confirms that the antibody activity was conserved, and that the antigen can be determined in the presence of a complex matrix as well.

The invention claimed is:

1. A method of surface modification by proteins for analyte preconcentration for desorption-ionization mass spectrometry techniques and immunochemical assays characterized by that a carrier gas under pressure 0.05-0.5 MPa and a stock solution of a protein to be sprayed are introduced into an enclosed compartment that is at voltage [±(200-8000) V], wherein a formed charged aerosol exiting from the electrospray is introduced into an evaporation compartment preheated to the temperature of 30° C. to 80° C., and the exiting dried aerosol is introduced onto a surface for modification, which is placed after the evaporation compartment.

2. The method of surface modification for analyte preconcentration for desorption-ionization mass spectrometry techniques and immunochemical assays according to claim 1 characterized by that the surface for modification is conductive having the dry material resistivity lower than 1020 Ω·m and is at voltage [±(200-5000) V] of the polarity opposite to the voltage of the electrospray.

3. The method of surface modification according to claim 1 or claim 2 characterized by that a mask, which is at voltage [±(200-5000) V] of the polarity opposite to the voltage of the electrospray, is placed between the evaporation compartment and the surface for modification, at the distance of 3 mm from the surface for modification.

4. The method of surface modification according to claim 1 characterized by that the temperature of the carrier gas is in the range of 30° C. to 80° C.

5. The method of surface modification according to claim 1 characterized by that the sprayed protein is selected from the group comprising an enzyme, lectin or an antibody.

6. The method of surface modification according to claim 5 characterized by that the enzyme is selected from the group comprising oxidoreductase, transferase, hydrolase, lyase, isomerase, ligase, or protease, preferably trypsin, pepsin; lectin is selected from the group comprising concanavalin A, lectin from cereal germs or peanuts, ricin, or lentil lectin; the antibody is selected from the group comprising immunoglobulins of the classes of IgA, IgG, IgD, IgE, or IgM, preferably antileptin antibody or FGF 21 antibody.

7. The method of surface modification according to claim 1 characterized by that the concentration of the sprayed protein in the stock solution is in the range of 0.01 to 100 μmol/L.

8. The method of surface modification according to claim 1 characterized by that the stock solution is an aqueous solution or a mixture of water and at least one organic solvent, preferably methanol or acetonitrile.

9. The method of surface modification according to claim 8 characterized by that the stock solution further comprises a buffer of the concentration of 1 μmol/L to 1 mol/L.

10. The method of surface modification according to claim 8 or claim 9 characterized by that the content of the organic solvent in the mixture is up to 80% v/v.

11. The method of surface modification according to claim 1 or claim 4 characterized by that the carrier gas is selected from the group comprising nitrous oxide, nitrogen, carbon dioxide, helium, neon, argon, krypton, xenon, or oxygen.

12. The method of surface modification according to claim 1 or claim 2 characterized by that the surface for modification is selected from the group comprising a thermally stable metal, glass, silicon nanostructures, carbon nanotubes, graphene, and a thermally and mechanically stable synthetic polymer.

* * * * *

UNITED STATES PATENT AND TRADEMARK OFFICE
CERTIFICATE OF CORRECTION

PATENT NO. : 10,180,435 B2  
APPLICATION NO. : 15/511680  
DATED : January 15, 2019  
INVENTOR(S) : Petr Novak et al.

It is certified that error appears in the above-identified patent and that said Letters Patent is hereby corrected as shown below:

In the Specification

Column 1,
Line 52, "Compare" should be -- Compared --.

Column 3,
Line 27, "lost" should be -- loss --.

Column 4,
Line 48, "results" should be -- result --.

Column 5,
Line 15, "opposite to of the obtained ions," should be -- opposite of the obtained ions, --.

Column 7,
Line 11, "is defined" should be -- are defined --.

Column 8,
Line 57, "compare" should be -- compared --.

Signed and Sealed this
Twenty-sixth Day of March, 2019

Andrei Iancu
*Director of the United States Patent and Trademark Office*